(12) United States Patent
Nikiforov

(10) Patent No.: US 6,720,148 B1
(45) Date of Patent: Apr. 13, 2004

(54) METHODS AND SYSTEMS FOR IDENTIFYING NUCLEOTIDES BY PRIMER EXTENSION

(75) Inventor: Theo T. Nikiforov, San Jose, CA (US)

(73) Assignee: Caliper Life Sciences, Inc., Mountain View, CA (US)

(*) Notice: Subject to any disclaimer, the term of this patent is extended or adjusted under 35 U.S.C. 154(b) by 16 days.

(21) Appl. No.: 10/079,134

(22) Filed: Feb. 20, 2002

Related U.S. Application Data
(60) Provisional application No. 60/270,667, filed on Feb. 22, 2001.

(51) Int. Cl.[7] ............... C07H 21/04; C12Q 1/68
(52) U.S. Cl. ............... 435/6; 435/91.2; 435/91.1; 536/23.1; 536/24.3; 536/25.32
(58) Field of Search ............... 436/6, 91.2, 91.1; 536/23.1, 24.3, 25.32

(56) References Cited

U.S. PATENT DOCUMENTS

| | | |
|---|---|---|
| 4,390,403 A | 6/1983 | Batchelder |
| 4,908,112 A | 3/1990 | Pace |
| 5,126,022 A | 6/1992 | Soane et al. |
| 5,498,392 A | 3/1996 | Wilding et al. |
| 5,571,410 A | 11/1996 | Swedberg et al. |
| 5,585,069 A | 12/1996 | Zanzucchi et al. |
| 5,603,351 A | 2/1997 | Cherukuri et al. |
| 5,635,358 A | 6/1997 | Wilding et al. |
| 5,637,469 A | 6/1997 | Wilding et al. |
| 5,639,611 A * | 6/1997 | Wallace et al. ............... 435/6 |
| 5,699,157 A | 12/1997 | Parce |
| 5,750,015 A | 5/1998 | Soane et al. |
| 5,800,690 A | 9/1998 | Chow et al. |
| 5,869,004 A | 2/1999 | Parce et al. |
| 5,876,675 A | 3/1999 | Kennedy |
| 5,880,071 A | 3/1999 | Parce et al. |
| 5,882,465 A | 3/1999 | McReynolds |
| 5,885,470 A | 3/1999 | Parce et al. |
| 5,888,819 A | 3/1999 | Goelet et al. |
| 5,908,755 A * | 6/1999 | Kumar et al. ............... 435/6 |
| 5,942,443 A | 8/1999 | Parce et al. |
| 5,948,227 A | 9/1999 | Dubrow |
| 5,955,028 A | 9/1999 | Chow |
| 5,958,694 A | 9/1999 | Nikiforov |
| 5,959,291 A | 9/1999 | Jensen |
| 5,965,410 A | 10/1999 | Chow et al. |
| 5,976,336 A | 11/1999 | Dubrow et al. |

(List continued on next page.)

FOREIGN PATENT DOCUMENTS

| | | |
|---|---|---|
| WO | WO 9604547 | 2/1996 |
| WO | WO 9702357 | 1/1997 |
| WO | WO 9914226 | 3/1999 |

OTHER PUBLICATIONS

Markiewicz et al. "A new method of synthesis of fluorescently labelled oligonucleotides and their application in DNA sequencing." Nucleic Acids Research. vol. 25, No. 18, pp. 3672–3680, 1997.*

(List continued on next page.)

*Primary Examiner*—Jeffrey Fredman
*Assistant Examiner*—Jeanine Goldberg
(74) *Attorney, Agent, or Firm*—Andrew L. Filler

(57) ABSTRACT

The methods and systems for identifying nucleotides monitor changes in fluorescent signal that occur during the polymerase-mediated extension of dye labeled primer molecules. In certain aspects, the methods monitor changes in a fluorescent signal, e.g., relative polarization, emitted from a reaction mixture that contains a dye labeled primer that hybridizes to a target sequence such that the primer ends at the position of interest. Perfect hybridization at the position results in extension of the primer while imperfect hybridization, e.g., a mismatch at the position of interest results in no extension reaction. The occurrence of extension reaction is monitored by a change in the fluorescent signal of the mixture.

9 Claims, 7 Drawing Sheets

U.S. PATENT DOCUMENTS

| | | | |
|---|---|---|---|
| 5,989,402 | A | 11/1999 | Chow et al. |
| 6,001,231 | A | 12/1999 | Kopf-Sill |
| 6,012,902 | A | 1/2000 | Parce |
| 6,042,709 | A | 3/2000 | Parce et al. |
| 6,074,725 | A | 6/2000 | Kennedy |
| 6,100,541 | A | 8/2000 | Nagle et al. |
| 6,180,408 | B1 * | 1/2001 | Kwok et al. ............... 436/6 |
| 6,221,226 | B1 | 4/2001 | Kopf-Sill |

OTHER PUBLICATIONS

See et al. "Electrophoretic detection of single–nucleotide polymorphisms." Biotechniques. vol. 28, No. 4, pp. 710–716, Apr. 2000.*

Chen et al. "Fluorescence energy transfer detection as a homogeneous DNA diagnostic method." PNAS. vol. 94, pp. 10756–10761, Sep. 1997.*

Newton et al. "Analysis of any point mutation DNA." Nucleic Acids Research. vol. 17, No. 7, pp. 2503–2516, 1989.*

Cohen, C.B. et al., "A Microchip–Based Enzyme Assay for Protein Kinase A," *Anal. Chem.* (1999) 273:89–97.

Dasgupta, P.K. et al., "Electroosmosis: A Reliable Fluid Propulsion System for Flow Injection Analysis," *Anal. Chem.* (1994) 66:1792–1798.

Harrison, D.J. et al., "Capillary Electrophoresis and Sample Injection Systems Integrated on a Planar Glass Chip," *Anal. Chem.* (1992) 64:1926–1932.

Harrison, D.J. et al., "Towards Miniaturized Electrophoresis and Chamical Analysis Systems on Silicon: an Alternative to Chemical Sensors," *Sensors and Actuators B* (1993) 10:107–116.

Harrison, D.J. et al., "Micromachining a Miniaturized Capillary Electrophoresis–Based Chemical Analysis System on a Chip," *Science* (1993) 261:895–897.

Harrison, D.J. et al., "Integrated Electrophoresis Systems for Biochemical Analyses," *Sensors and Actuators* (1994) 21–24.

Jacobson, S.C. et al., "Fused Quartz Substrates for Microchip Electrophoresis," *Anal. Chem.* (1995) 67:2059–2063.

Kondo, H. et al., *Biotechniques* (2000) 29:868–872.

Manz, A. et al., "Electroosmotic and electrophoretic separations for miniaturized chemical analysis systems," *J. Micromech. Microeng.* (1994) 4:257–265.

Ramsey, J.M. et al., "Microfabricated chemical measurement systems," *Nature Med.* (1995) 1:1093–1096.

Sundberg, S., "High–throughput and ultra–high–throughput screening: solution– and cell–based approaches," *Current Opinions in Biotechnology* (2000) 11/47–53.

Seiler, K. et al., "Planar Glass Chips for Capillary Electrophoresis: Repetitive Sample Injection, Quantitation, and Separation Efficiency," *Anal. Chem.* (1993) 65:1481–1488.

Seiler, K. et al., "Electroosmotic Pumping and Valveless Control of Fluid Flow Within a Manifold of Capillaries on a Glass Chip," *Anal. Chem.* (1994) 66:3485–3491.

* cited by examiner

METHODS AND SYSTEMS FOR IDENTIFYING NUCLEOTIDES BY PRIMER EXTENSION

CROSS-REFERENCE TO RELATED APPLICATION

This application is related to U.S. Provisional Patent Application No. 60/270,667, filed Feb. 22, 2001, which is incorporated herein by reference in its entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Genotype analysis has taken a more prominent position in the sphere of biological research, and particularly in the worlds of diagnostic and pharmaceutical research. In particular, the analysis of genotypes of individual members of the population is believed to be predictive of those individual's predisposition to various diseases, as well as that individual's responsiveness, sensitivity, etc. to therapies for diseases or other conditions. As such, genotype analysis is believed to have important application in both diagnostic and therapeutic applications. Of particular interest is the identification of different polymorphic variations in the genetic material of the members of a population, and the relationship of those polymorphic variations to disease predisposition or sensitivity to pharmaceutical therapy. For example, identifying which variant of a large number of different polymorphisms within a patient would be applied to determine the proper course of therapy for an individual, or to genetically counsel an individual to avoid high-risk behavior for a given disease for which that individual might be predisposed.

A wide variety of different technologies or different applications of similar technologies have been proposed and demonstrated for the identification of particular genetic variations as well as discrimination of those variations among members of the population. For example, arrays of oligonucleotide probes have been employed to effectively re-sequence portions of a target sequence known to contain a polymorphic locus. Such methods rely upon the differential hybridization of the target sequence to different probes on an array. While generally effective, such methods are very costly in terms of equipment and arrays, and are of relatively low throughput, permitting one or only a few experiments to be performed on an array at any given time.

U.S. Pat. No. 5,888,819 describes a method by which a probe that is hybridized to the polymorphic locus is extended by one base over the locus. The extension incorporates a base having a distinguishable label associated with it, allowing identification of the incorporated base, and thus identification of the variation.

A variety of other similar methods are available that use target specific probes at or near the variant locus, and give a detectable signal if and when perfect or imperfect hybridization occurs, e.g., through the exonuclease mediated activation of a FRET pair dye, e.g., through cleavage of one member of the pair from the probe. Such methods include TaqMan® and Invader™ based technologies, available from Applied Biosystems, Inc. and Third Wave Technologies, Inc., respectively.

While all of the above methods are useful in polymorphism discrimination, such methods all suffer from problems of expensive reagents, equipment, or complex processes. Accordingly, it would be desirable to provide a discrimination method that is relatively simple, inexpensive and which does not require extremely expensive equipment, while still providing relatively high throughput and accuracy.

SUMMARY OF THE INVENTION

The present invention provides novel, simplified methods of identifying a nucleotide in a particular position of interest in an oligonucleotide sequence. The methods and systems are particularly useful in identifying polymorphic variants in genetic material, e.g., SNPs, STRs, deletions, insertions, and the like.

In a first aspect, the present invention provides methods of identifying a nucleotide in at least a first position in a polynucleotide sequence. In these methods, a polynucleotide target sequence is provided. The target sequence is hybridized with a first oligonucleotide probe, wherein the probe comprises a first subsequence of nucleotides, a first terminal nucleotide, and a first fluorescent label. The subsequence is complementary to a portion of the target sequence that is immediately adjacent to the first position, and the terminal nucleotide is complementary to one possible nucleotide in the first position. The hybridized probe and target sequence are then contacted with polymerase extension reagents in a first extension reaction mixture. By monitoring a fluorescent signal from the hybridizing and contacting steps one can identify the presence or absence of polymerase extension of the probe, the presence of polymerase extension of the probe indicating that the terminal nucleotide is complementary to the nucleotide in the first position. From that determination, one can identify the nucleotide in the first position.

The present invention also provides systems for carrying out these methods. Specifically, in at least one aspect of the invention there is provided a system for identifying at least a first oligonucleotide in a target nucleic acid sequence. The system comprises a reaction vessel having a first target nucleic acid sequence having an unknown nucleotide at a first position disposed in it. Also included is a first oligonucleotide probe having a first subsequence of nucleotides, the first subsequence being complementary to a subsequence of nucleotides in the target sequence that are immediately adjacent to the first position, a terminal nucleotide that is positioned to be adjacent to the first position when the first subsequence of the probe is hybridized to the subsequence of the target, and a fluorescent label. Further included are polymerase extension reagents. The system also includes a detector configured to monitor a fluorescent signal from the reaction vessel that is indicative of a presence or absence of polymerase extension of the probe.

DETAILED DESCRIPTION OF THE INVENTION

The present invention is generally directed to novel methods and systems for identifying nucleotide bases in polynucleotide sequences. In particular, the methods described herein, and the systems that implement such methods, combine a probe hybridization step with a polymerase extension reaction and novel detection strategies to yield a method by which a nucleotide base at a particular position in a target nucleic acid sequence can be identified in a homogeneous reaction, e.g., without the need for multiple different operations, i.e., separation/purification steps.

The methods and systems of the invention are particularly useful in any instance where one is desirous of knowing the identity of a nucleotide at a given position in a target nucleic acid sequence. While such methods could be used to identify long sequences of nucleotides, the methods are particularly well suited to single-base identification, such as discrimination of single base or several base mutations in a known target sequence, e.g., single base deletions, insertions or polymorphisms (SNPs), short tandem repeats (STRs) or the like.

Figure 1:
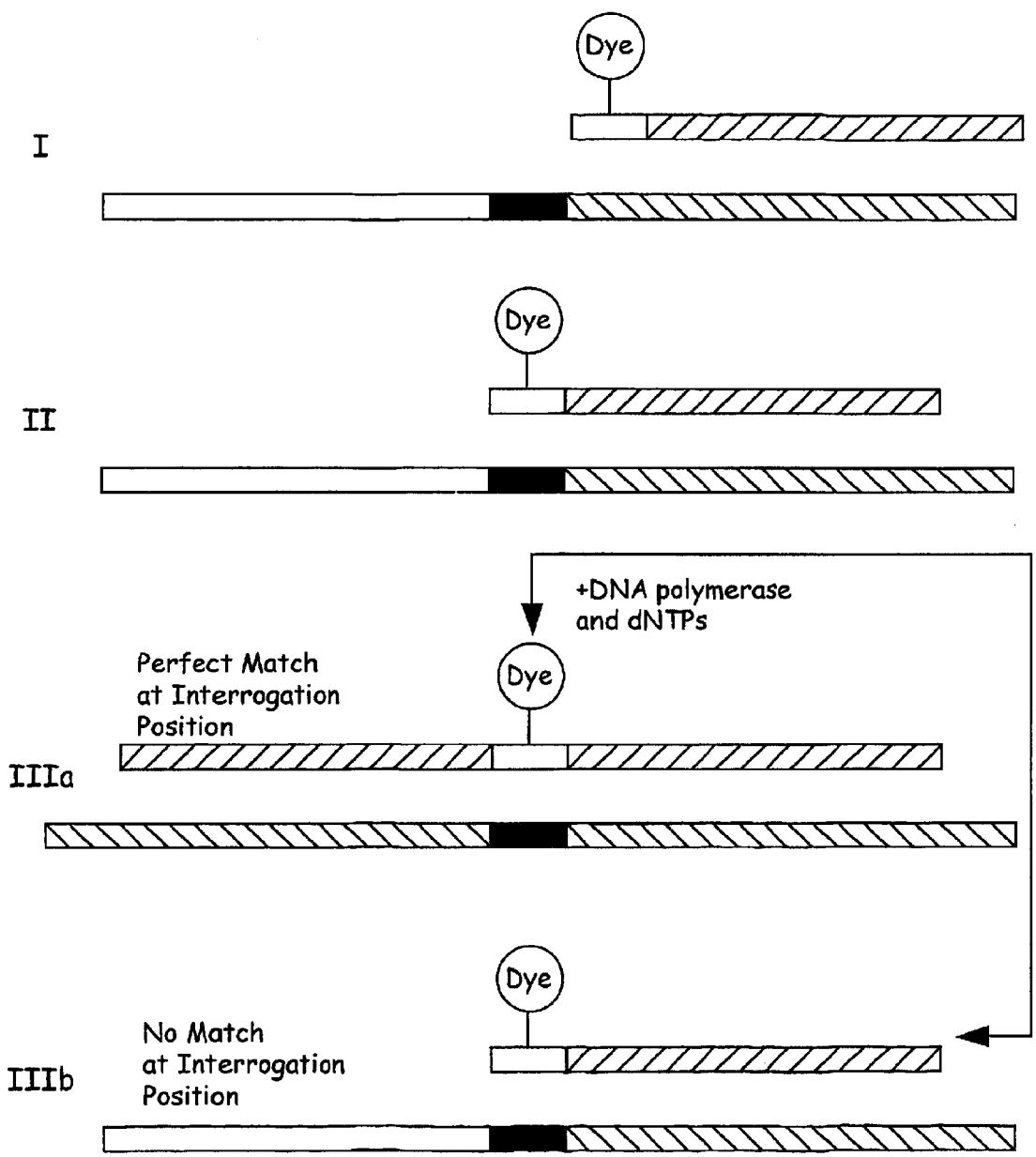
FIG. 1 is a schematic illustration of the detection methods of the present invention.

In general, the methods of the invention employ an oligonucleotide probe sequence that is labeled with a detectable label, preferably a fluorescent label. An exemplary method of the invention is schematically illustrated in FIG. 1. As shown in panel I, the probe sequence includes a subsequence of nucleotides (shown as the hatched portion) that are selected so as to be complementary to a portion of the target sequence (shown by opposite hatching) that is immediately adjacent to the position in the target sequence that is sought to be identified (shown in black). The probe is also configured to include an interrogation base (shown by the unfilled portion of the probe) at one of its terminal positions such that the interrogation base will be opposite the position in the target sequence that is sought to be identified when the probe and target are hybridized. The interrogation base is preferably at the 3'-terminal position of the probe. As shown, the interrogation base is also labeled with a detectable dye, e.g., a fluorescent moiety. The interrogation base can be any one of the four bases, e.g., A, T, G or C. By way of example, where one is attempting to identify which allele is present in a position of the target sequence that is known to have two possible alleles, e.g. a single nucleotide polymorphism (SNP), the interrogation base will be selected to be complementary to one of those alleles.

As shown in Panel I and II, the labeled probe is contacted with the target sequence under conditions that permit hybridization between the probe and the complementary portion of the target polynucleotide sequence. Where the interrogation base is complementary to the position of interest in the target sequence, the probe and target will form a perfectly matched hybrid. Where the interrogation base in the probe is not complementary to the position of interest in the target, then the probe/target hybrid will have a single base mismatch at the terminal position of the probe. In either event, the labeled probe is hybridized to the target sequence.

As shown in Panels IIIa and IIIb, the labeled oligonucleotide probe/target is then exposed to polymerase extension reagents, e.g., a DNA polymerase enzyme and dNTPs, which are intended to extent the probe sequence from the terminal interrogation base. As noted above, since the terminal interrogation base is disposed at the 3' terminus of the probe, the polymerase is preferably a 5'-3' polymerase. Examples of particularly preferred DNA polymerases include Klenow fragment, exonuclease minus Klenow, Taq polymerase, Thermosequenase (available from APBiotech, Inc.), or the like. In the case where the probe/target hybrid is a perfect match, e.g., the interrogation base is complementary to the position of interest in the target, the extension reaction will occur as illustrated in Panel IIIa. However, where the interrogation base is not complementary to the position of interest, no extension reaction will occur, as shown in Panel IIIb).

In accordance with the present invention, identification of the nucleotide at the position of interest is carried out by identifying whether extension of the labeled probe occurs. As noted, where the interrogation base is complementary to the position of interest, then the labeled probe is extended. Where the two bases are not complementary, then the labeled probe is not extended. As will be clarified further below, in some cases, proofreading polymerase enzymes may be able to extend a mismatched probe, but would do so by excising the terminal interrogation base and replacing it with a complementary base. In those cases where such enzymes are employed, the label on the probe is disposed on the terminal interrogation base, such that the label is excised from the extended probe, and a "labeled" probe is not extended. As such, while proofreading polymerases are used in conjunction with the present invention, it is generally preferred to use non-proofreading enzymes, e.g., that lack exonuclease activity.

Thus, if the labeled probe is extended (as the labeled probe), one can identify the nucleotide in the position of interest as that nucleotide that is complementary to the interrogation nucleotide. If it is not extended, then the process is repeated with different probes that have different bases in the interrogation position, until extension is seen and the nucleotide in the position of interest can be identified.

Typically, in order to determine if the extension reaction had occurred, one would subject the reaction mixture to a separation process and identify whether the labeled product was the size of the probe, or the size of an extension reaction product. However, as noted previously, this requires a substantial increase in the complexity of the overall process, in that it requires at least a separation step, e.g., electrophoretic separation. The present invention, on the other hand, takes advantage of the surprising discovery of a novel detection strategy that permits in situ detection of the extension reaction from the homogeneous reaction mixture, providing a substantial reduction in complexity and time requirements. In particular, it has been discovered that occurrence of the extension reaction on the labeled probe results in both a decrease in the level of fluorescence polarization of the hybrid, as well as an increase in the level of fluorescent intensity emitted by the labeled hybrid during the extension reaction. In one aspect, it is surprising that one could utilize fluorescence polarization detection to distinguish the extended labeled probe/target hybrid from the unextended probe/target hybrid, as both species are of similar size, and would have similar rotational diffusion rates. It is further surprising that the marginally larger species, namely the extended probe/target hybrid, would have reduced fluorescence polarization as compared to its unextended counterpart, as fluorescence polarization level should increase with size and concomitant decreased rotational diffusion rate. It is also particularly surprising that the extended species has reduced polarized fluorescence levels as compared to the unextended counterpart, even in the presence of a proofreading polymerase enzyme. For a discussion of effects of 3' fluorescently labeled probes on exonuclease activity in mismatched probes, see H. Kondo et al., Biotechniques 29:868–872 (2000).

Equally surprising is the discovery that as the labeled probe is extended, the homogeneous reaction mixture has increased fluorescent intensity. Again, this is surprising in that the level of fluorescent label in the homogeneous reaction mixture remains constant.

As noted briefly above, the methods and systems described herein are useful in identifying one or more bases in a target nucleic acid sequence. Such methods are particularly well suited to identifying variant bases in known sequences of nucleic acids, such as single nucleotide polymorphisms (SNPs) where a given sequence position ("locus") may be occupied by one or more different bases ("alleles") in different members of the population. Similarly, other variations in the known sequence are also readily identified and characterized using these methods, including point mutations such as single base insertions and deletions, short tandem repeats (STRS) and the like.

In the case of these variants, the variant sequence position is the nucleotide of interest. The probe sequence is selected to be complementary to the portion of the target sequence that is immediately adjacent to the position of interest. The terminal position on the probe, and typically the 3' terminal position of the probe is occupied by the interrogation base. In the case where the sequence position of interest is known to be occupied by one of two different nucleotides, then the interrogation base is selected to be complementary to one of those nucleotides.

Typically, a control experiment is also run on the target sequence using an interrogation base that is complementary to the other variant, so as to provide a proper basis for comparison, e.g., providing a negative control. In certain instances, it is desirable to interrogate the target sequence with probes complementary to both variants simultaneously, in the same reaction mixture to provide optimal control and throughput. This is generally accomplished by providing each different probe with an optically different label, e.g., having different fluorescent characteristics such as excitation and/or emission spectra, and detecting the extension reaction using distinguishing detection optics, as described in greater detail below.

Where the position of interest potentially occupies any one of the four bases, probes are used that include all four different interrogation bases. Again, these are contacted with the target sequence either in four separate reactions, or simultaneously in one, two or three different reactions, using multiple different probes to separately detect the various hybridization reactions, or lack thereof.

The probe sequences used in conjunction with the methods of the present invention are typically relatively short as compared to the target nucleic acid sequence, but are long enough to provide confidence that the probe is only complementary to one portion of the target sequence. As such, the probes, including the interrogation base, ate typically between about 10 and about 50 nucleotides in length, preferably, they are from about 15 to about 30 nucleotides in length and more preferably, from about 18 to about 25 nucleotides in length. Further, although described in terms of "nucleotides," e.g., ribonucleic acid and deoxyribonucleic acid monomers, it will be appreciated that in many instances, and in certain preferred aspects, the probes are made up in whole or in part from monomers that are nucleic acid analogs. For example, in certain preferred aspects, the probes are constructed of locked nucleic acid monomers (LNAs), which include bi or tricyclic nucleic acid analogs. These analogs have a number of structural and performance advantages over natural nucleic acids, e.g., DNA and RNA, including improved hybridization characteristics (see, Published International Patent Application No. WO 99/14226, which is incorporated herein by reference in its entirety for all purposes). A variety of different analogs may be employed in place or in addition to natural nucleic acid monomers or the analogs specifically described above.

As noted above, the probe sequence comprises a first subsequence of nucleotides that is complementary to a portion of the target nucleic acid sequence that is adjacent to the nucleotide position of interest in the target sequence. The probe also includes an interrogation base at its terminal position, preferably the 3' terminal position, which, when the probe and target are hybridized, is positioned adjacent to the position of interest, such that if the interrogation probe and the position of interest are complementary, they too will hybridize (See FIG. 1).

In addition to the subsequence and interrogation nucleotide, the probes will also include a detectable labeling group, referred to generally as a label. Typically, the label will comprise a group or moiety that fluoresces when exposed to light of a certain wavelength. A wide variety of different fluorescent labeling moieties may be employed on the probes for use in accordance with the present invention. For example, in certain cases, the probe has a fluorescein group coupled to one base in its sequence., Different labeling groups may be employed in instances where multiplexed assays are desired, e.g., labels that are distinguishable by their fluorescent characteristics, e.g., excitation or emission profiles. This allows distinguishing multiple different labeled probes within the same reaction mixture. A large number of different labeling groups having a wide variety of differing fluorescent characteristics are well known, and are generally commercially available from, e.g., Molecular Probes, Eugene, Oreg., and are described in detail in the Handbook of Fluorescent Probes and Research Chemicals (Molecular Probes Inc., Sixth Ed. 1998, and Supps.), the full content of which is incorporated herein by reference in its entirety for all purposes.

As used herein, the target sequence may comprise any nucleic acid sequence in which one has a desire to identify a given nucleotide. Typically, such sequences are obtained and/or derived from nucleic acid samples of virtually any organism that is the subject of study. Such samples may be derived or obtained from mammalian, bacterial, viral, fungal, plant, insect or other sources depending upon the researchers desire. In particularly preferred aspects, the methods are employed in genotyping experiments and are preferably derived from mammalian, bacterial, plant or fungal genomic material. Of most notable interest are mammalian genotyping methods. The target sequences may be directly obtained from the source organism, or they may be subjected to certain preparation, enrichment and/or partitioning steps, e.g., amplification, etc. In the case of amplified target sequences, e.g., amplified using polymerase mediated PCR amplification, carrying out the dye-labeled primer extension methods described herein can involve simply adding the dye labeled primer to the amplified reaction mixture. In particular, the excess polymerase and nucleoside triphosphates from the amplification reaction are once again employed in the extension of the dye-labeled primer. This is useful in allowing the overall process of amplifying genomic DNA and genotyping the target within a single reaction vessel, simply by adding the primer reagent following the amplification reaction.

As noted above, in preferred aspects, the methods of the present invention optionally employ fluorescence intensity detection or fluorescence polarization detection. In either event, detection systems typically include a light source that produces light of a desired wavelength for the labeling groups that are employed. Light from that source is directed through an optical train, e.g., lenses and filters, toward the sample material that is being analyzed, e.g., in a well, reaction chamber, capillary/fluidic channel, or the like. Emitted fluorescence is typically collected back through the same optical train, and differentially directed toward a light detector for quantitation of the light that is due to fluorescence. Appropriate filters are used to separate reflected excitation light from fluorescent emissions, as well as separating fluorescent emissions having different properties, e.g., wavelengths or polarization levels.

The systems that are used to practice the above-described methods typically employ a reaction vessel in which the target sequence, probes, and extension reagents are combined, and a detection system for monitoring a change in the fluorescent signal emitting from the reaction mixture, disposed in sensory communication with the reaction vessel.

Figure 3:
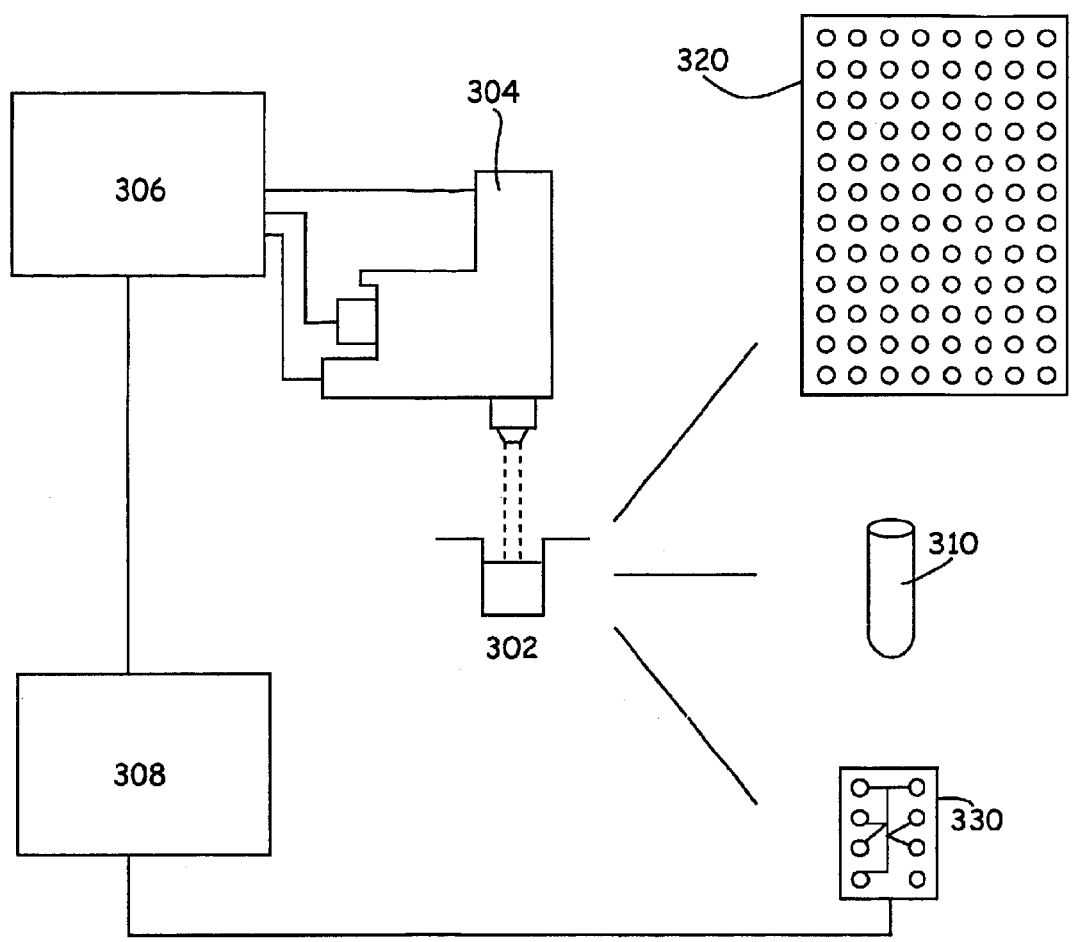
FIG. 3 schematically illustrates an overall system for use in carrying out the methods of the invention.

A schematic illustration of a system for use in conjunction with the methods described herein is illustrated in FIG. 3. As shown the system includes a reaction vessel 302, a detector 304 that is disposed in sensory communication with the reaction vessel, and a computer or processor 306, operably coupled to the detector.

As shown, the reaction vessel is optionally selected from a simple test tube 310 or reaction well 320 in a multiwell plate. Alternatively, the reaction vessel may include a capillary tube, or a fluidic channel or channels in a microfluidic device 330.

In the case of test tubes or reaction wells in a multiwell plate, the various reagents are generally pipetted into the vessel in appropriate proportions to carry out the methods described herein. The reaction mixture is then subjected to detection by directing the detector at that mixture, either directly, e.g., through an opening in the vessel, or through a transparent wall of the vessel.

In preferred aspects, a microfluidic device is used to carry out the methods described herein. In particular, microfluidic devices that incorporate integrated channel networks can be readily used to store, move, mix, react and separate reaction components with relative ease, reproducibility and speed. With reference to the present described methods for example, microfluidic devices are optionally provided with reservoirs that hold the various reagents that are used in the methods. The different reagents are transported from their reservoirs to a common reaction channel for mixing, extension and detection. In the case of microfluidic devices, the systems of the invention optionally include a flow controller 308 operably coupled to the microfluidic device. The controller applies one or more driving forces to move fluids and/or other materials through the various channels of the microfluidic device 330, in accordance with a desired flow pattern, e.g., to mix, separate, react, etc. The controller is typically coupled to the computer 306, which contains the programming that instructs the controller to provide those driving forces in accordance with a preprogrammed flow profile.

Figure 4:
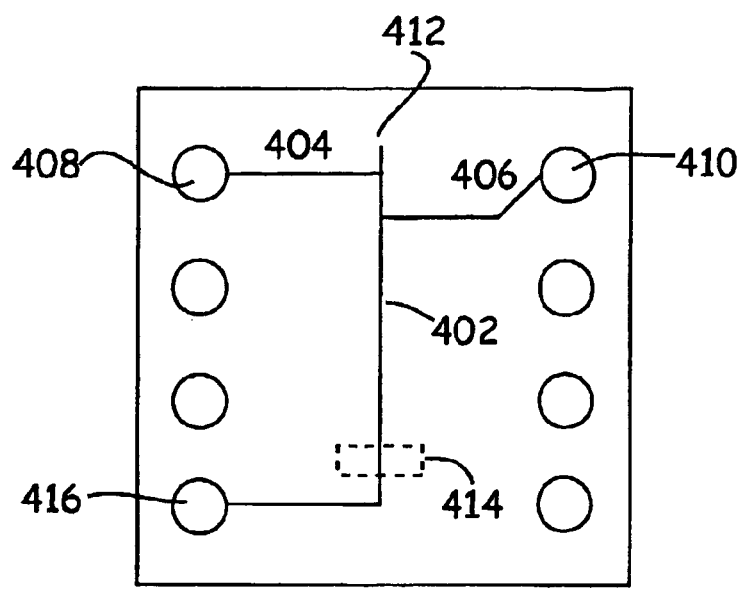
FIG. 4 schematically illustrates a microfluidic device that is optionally used as a reaction vessel in the present invention.
Figure 4:
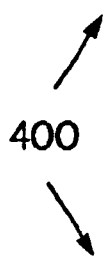

One example of a microfluidic device for use in such methods is shown in FIG. 4 from a top and side view. As shown, the microfluidic device 400, includes a channel network that is made up of at least one reaction channel 402. Side channels 404 and 406 are used to transport reagents from reservoirs 408 and 410, respectively, to the reaction channel 402. For example, the dye labeled primer sequence can be deposited into reservoir 410. Similarly, extension reagents, e.g., polymerase enzyme and dNTPs are optionally stored in, e.g., reservoir 408, and materials from each reservoir are controllably transported into the reaction channel or chamber. The target sequence, e.g., a PCR product, is then drawn into the reaction channel from sources external to the microfluidic device, e.g., a multiwell plate, LibraryCard™ reagent array (see, U.S. Pat. No. 6,042,709), or the like. Accession of the externally stored reagents is via a capillary sampling element 420 that is coupled to the microfluidic device. In particular, the capillary 420 includes a channel disposed through it, which channel connects to channel 402 at junction 412. Target drawn into the capillary is then moved through junction 412 into the channel 402. Within reaction channel 402, the various reagents are combined to carry out the methods described herein. The results are then detected within that channel, e.g., through the transparent surface of the microfluidic device at detection zone 414. It will be appreciated upon reading the examples provided herewith that in the case of typing experiments from PCR reaction products, the polymerase and dNTPs used in that amplification can serve double duty by performing the dye labeled primer extension reaction. As such, following an amplification reaction, one may simply add the dye labeled primer to the reaction mix, and begin monitoring the fluorescence polarization level of the mixture. This results in an extremely simplified reaction protocol for identifying single nucleotide changes in a target sequence.

Movement of materials through microfluidic channel networks is generally accomplished by one or more of a number of different methods. For example, in its simplest aspects, a pressure based flow is used to drive fluids and other materials through the various channels of the device. Such pressure based flow may be applied via multiple pressure sources coupled to the reservoirs of the device, and individually actuated to drive flow in one or more channels at one or more different rates. In particular, multiple pressure pumps are optionally coupled to each of reservoirs 408, 410 and 416, and apply pressures or vacuums to achieve a desired flow rate within the channel associated with that reservoir.

Alternatively, channel networks are optionally or additionally engineered whereby a single pressure or vacuum applied to one or more reservoirs in the device yields a particular set of desired flow profiles in the various different channels of the device. By way of example, in the case of the channel network shown in the device of FIG. 4, the main channel 402, side channels 404 and 406, and the capillary 420 are each engineered such that when a single vacuum is applied to waste reservoir 416, reagents flow into reaction channel 402, from reservoirs 408, 410 and the capillary at a desired ratio. Such engineering typically involves altering the resistance of the various channels to flow, relative to one another. This is generally accomplished by varying one or more of the length and/or cross sectional areas of the channels. Alternatively, flow resistance altering matrices, e.g., frits, filters, gels, etc., are incorporated into the various channels to adjust their relative resistance to flow. Engineering of channel networks in this manner is generally described in U.S. Pat. No. 6,050,119, which is incorporated herein by reference in its entirety for all purposes.

When the reaction mixture passes through the detection zone, e.g., past detection window 414, a fluorescence polarization detector detects the level of polarized fluorescence. This level is compared to the level in the absence of the extension reaction, e.g., in a reaction mixture that lacks polymerase or that contains a known mismatched probe (negative controls). A significant change in fluorescence polarization, e.g., reduction, indicates that extension occurred.

As noted above, the detectors used in the systems described herein, e.g., the fluorescence based detectors, are disposed in sensory communication with the reaction vessel and particularly, the contents of the reaction vessel. As used herein, "disposed in sensory communication" refers to the positioning of the detector relative to the reaction vessel, such that the detector is capable of receiving a detectable signal from the reaction vessel or its contents. In the case of optical detectors, this typically entails placement of the detector's optical receiving element, e.g., a light collector, i.e., an objective lens, adjacent to an open or a transparent portion of the reaction vessel, such that an optical signal can freely pass from the reaction vessel's contents to be collected by the objective lens, and detected by the detector. Such sensory communication may also include other intermediate elements that are either integral to the vessel or are separate from both the detector and the vessel, including additional optical elements, such as spatial, chromatic, or other optical filters, wave guides, optical gratings, etc.

Figure 2A:
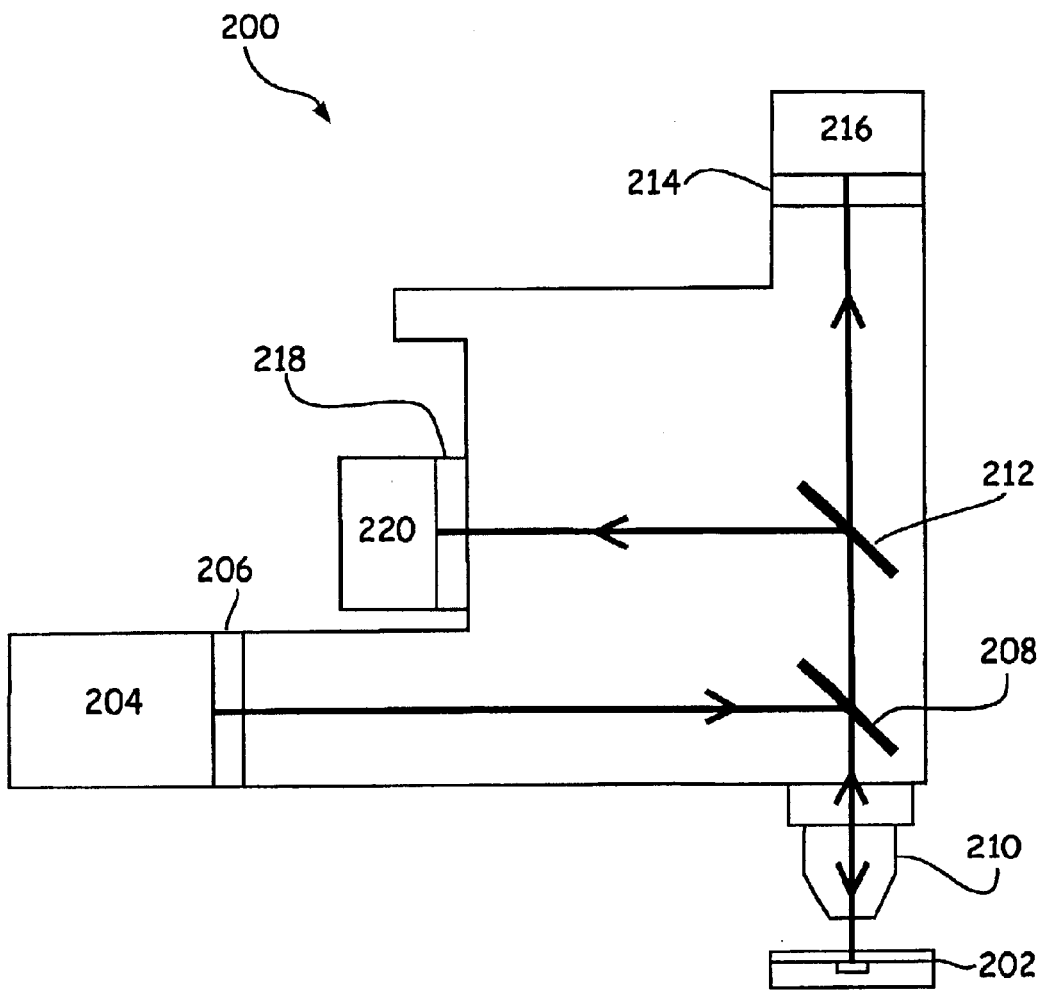
FIG. 2A is a schematic illustration of a fluorescence detector for monitoring fluorescence intensity, in accordance with certain aspects of the present invention.

A basic fluorescence detector module is shown in FIG. 2A. As shown, the detector 200 includes a light source 204, which is generally selected from a variety of different light sources, e.g., LEDs, laser diodes, lasers, arc lamps, and the like, where the light source is capable of generating light of an appropriate wavelength, e.g., to excite the fluorescently labeled sample material. Light from the light source is directed through an optical train, which, as shown, includes a dichroic mirror 208, which reflects the excitation light through an objective lens 210 and into the reaction vessel 202. Both reflected excitation light and emitted fluorescence are collected back through the objective lens 210 and directed to dichroic mirror 208. The reflected excitation light is again reflected by the dichroic mirror while the emitted fluorescence, having a different wavelength from the excitation light, passes through the dichroic mirror 208, and band pass filter 214 eventually to be detected by detector 216. As noted repeatedly herein, multiple differently fluorescing labels may be used in order to multiplex a given analysis. In those cases, an additional dichroic mirror 212 is provided to pass emitted fluorescence of a first wavelength to be detected by detector 216, while fluorescence of another wavelength is reflected onto detector 220, through filter 218. This allows simultaneous detection of multiple analyses, e.g., matched and mismatched hybridization/extension reactions.

Fluorescence polarization detection monitors the relative level of depolarized fluorescence that is emitted from a fluorescent compound when excited by a polarized excitation light source, which is dependent upon the relative rotational diffusion rate of the compound. The rotational diffusion rate of a compound in a given system is typically a function of the size of the compound. Briefly, when an immobilized fluorescent compound is excited by a polarized light source, that compound will fluoresce in the same plane as the activation light. In a fluid system where the compound is spinning and tumbling in space, the level of polarized fluorescence will be negatively impacted as that compound spins and tumbles faster, e.g., faster tumbling compounds will emit less polarized or more depolarized fluorescence. The rate of tumbling and spinning is referred to as the rotational diffusion rate of the compound. As the size of the fluorescent compound increases, it will typically rotate more slowly, resulting in emission of more polarized fluorescence. Thus, changes in size of the fluorescent compound, e.g., through the binding of the compound to another molecule, resulting in a larger complex, can be monitored by monitoring the relative level of polarized fluorescence emitted from the mixture.

Figure 2B:
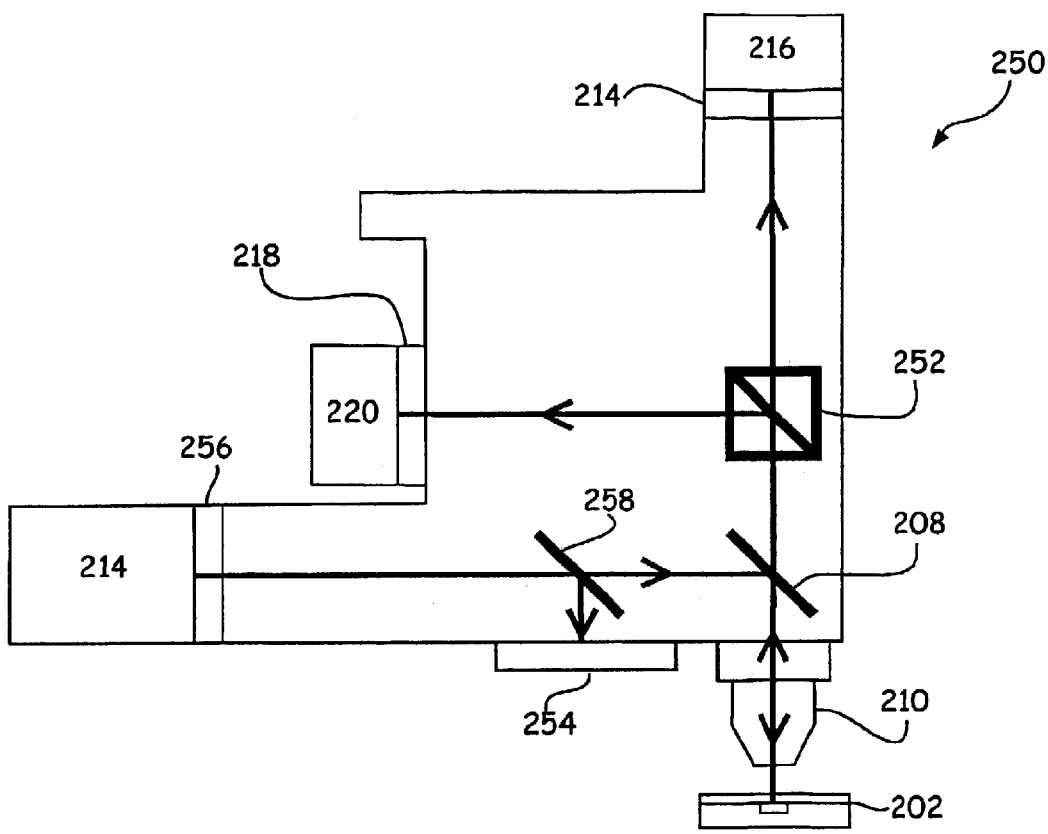
FIG. 2B is a schematic illustration of a fluorescence polarization detector for use with certain aspects of the present invention.

A schematic of a fluorescence polarization detection system is illustrated in FIG. 2B. As shown, the fluorescence polarization detector 250 includes a light source 204, which generates light at an appropriate excitation wavelength for the fluorescent compounds that are present in the assay system. Typically, coherent light sources, such as lasers, laser diodes, and the like are preferred because of the highly polarized nature of the light produced thereby. The excitation light is directed through an optional polarizing filter 256, which passes only light in one plane, e.g., polarized light. The polarized excitation light is then directed through an optical train, e.g., dichroic mirror 208 and microscope objective lens 210 (and optionally, reference beam splitter 258), which focuses the polarized light onto the sample receptacle (illustrated as a channel in microfluidic device 202), in which the sample to be assayed is disposed.

Fluorescence emitted from the sample is then collected, e.g., through the objective lens 210, and directed back through dichroic mirror 208, which passes the emitted fluorescence and reflects the reflected excitation light, thereby separating the two. The emitted fluorescence is then directed through a beam splitter 252 where one portion of the fluorescence is directed through a filter 214 that filters out fluorescence that is in the plane that is parallel to the plane of the excitation light and directs the perpendicular fluorescence onto a first light detector 216. The other portion of the fluorescence is passed through a filter 218 that filters out the fluorescence that is perpendicular to the plane of the excitation light, directing the parallel fluorescence onto a second light detector 220. In alternative aspects, beam splitter 252 is substituted with a polarizing beam splitter, e.g., a Glan prizm, obviating the need for filters 214 and 218. These detectors 216 and 220 are then typically coupled to an appropriate recorder or processor (not shown in FIG. 2B) where the light signal is recorded and or processed as set out in greater detail below. Photomultiplier tubes (PMTs), are generally preferred as light detectors for the quantification of the light levels, but other light detectors are optionally used, such as photodiodes, or the like.

As with the fluorescent intensity detection, multiple different wavelength specific filters are optionally employed in order to distinguish multiple different fluorescent labels in a single reaction mixture, allowing multiplexing of assay operations. In the case of genotyping experiments, such multiplexing includes simultaneous interrogation of a single locus with each of the different allele specific probes, each bearing a differently fluorescing label. Similarly, such multiplexing allows interrogating multiple different loci, each with a differently fluorescing probe. Detection systems that distinguish between the differently fluorescent probes are substantially as shown in FIGS. 2A and 2B, except that they include additional elements to the optical train that split off the fluorescence of different wavelengths, e.g., via a dichroic mirror or beam splitter, and separately detect that fluorescence using an additional detector element, e.g., photodiode or PMT.

As noted, the overall systems of the invention typically include a computer that is operably coupled to the detector, to receive the data from the detector and store it. The computer is also typically programmed to analyze the received data, and determine from that data the characterization of the assay results. For example, the computer typically analyzes the fluorescence data from the detector and determines whether the fluorescent signal is substantially changing or remaining substantially unchanged. By substantially changing is generally meant a deviation in the average fluorescent signal of greater than 5%, and typically, greater than 10%, and in certain cases, greater than 20%, 25% or even 50%. Typically, these thresholds are programmed into the computer, which then identifies and interprets these changes.

By way of example, in the case of fluorescence polarization based detection in the methods of the invention, the computer analyzes the received data to determine if the fluorescence polarization level has changed, e.g., decreased by more than a threshold level. Where the computer detects such a change, it indicates that the probe used was perfectly hybridized to the target, and from the sequence of the probe, the computer is able to correctly identify the nucleotide of interest in the target sequence. Optionally, in the case of assays that use, e.g., two probes for each locus that represent each potential allele at that locus, where the two probes have different fluorescent labels (e.g., distinguishable), the computer is programmed to receive both different fluorescent signals, and identify which between those two signals is the result of perfect hybridization, e.g., by a decrease in fluorescent polarization.

The computer is also optionally programmed to operate other elements of an overall system, including material transport systems for microfluidic devices, plate handling robotics and other equipment, etc.

EXAMPLES

Examples: SNP Discrimination by Extension of Dye-labeled Probe and Fluorescence Polarization Detection The above-described methods were used to identify single nucleotide alterations in target nucleic acid sequences
1. Sequences of Probes The following dye labeled primer probes were prepared:

| Probe # | Sequence |
|---|---|
| 425T | 5' CTGCCATTATGTTAGGCATTAX (SEQUENCE ID NO:1) |
| 425C | 5' CTGCCATTATGTTAGGCATTAY (SEQUENCE ID NO:2) |
| 213T | 5' AGGACTTCCACGTGGACCAGGX (SEQUENCE ID NO:3) |
| 213C | 5' AGGACTTCCACGTGGACCAGGXY (SEQUENCE ID NO:4) |

Where X is a fluorescein labeled thymidine residue, and Y is a fluorescein labeled cytosine residue. To synthesize these labeled probes, two modified CPGs were used (obtained from Glen Research). The modified CPG used for the probes containing a labeled T at the 3' end had the following structure:

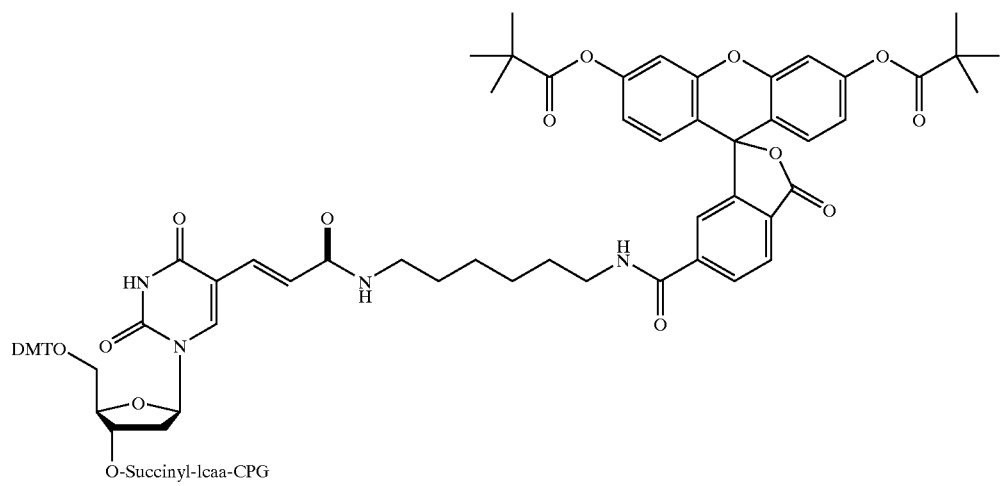

The modified CPG used to prepare probes with a labeled C at the 3' end had the following structure:

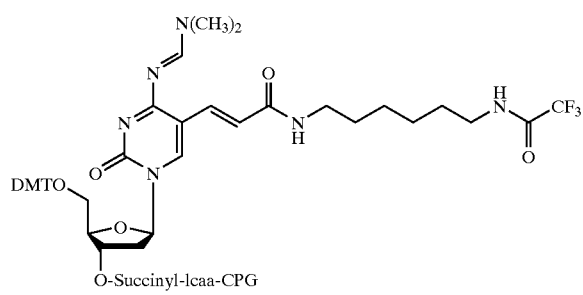

The probes containing a fluorescein labeled T at the 3' end were obtained directly, after ammonia cleavage and deprotection of the oligos from the CPG. On the other hand, the preparation of the probes having a fluorescein labeled C at the 3' end required a post-synthetic conjugation step, to attach the dye to the amino group obtained after the standard oligonucleotide deprotection.

The sequences of the DNA targets used with these probes were:

| Seq. #: | Sequence | SEQUENCE ID NO. | Used with probe # |
|---|---|---|---|
| 309 | 5'TTTGGCATGTAATGCCTAACATAATGGCAG | 5 | 425T, 425C |
| 310 | 5'TTTGGCATATAATGCCTAACATAATGGCAG | 6 | 425T, 425C |
| 311 | 5'ACGGTGGTCGCCTGGTCCACGTGGAAGTCCT | 7 | 213T, 213C |
| 312 | 5'ACGGTGGTCACCTGGTCCACGTGGAAGTCCT | 8 | 213T, 213C |

Figure 5A:
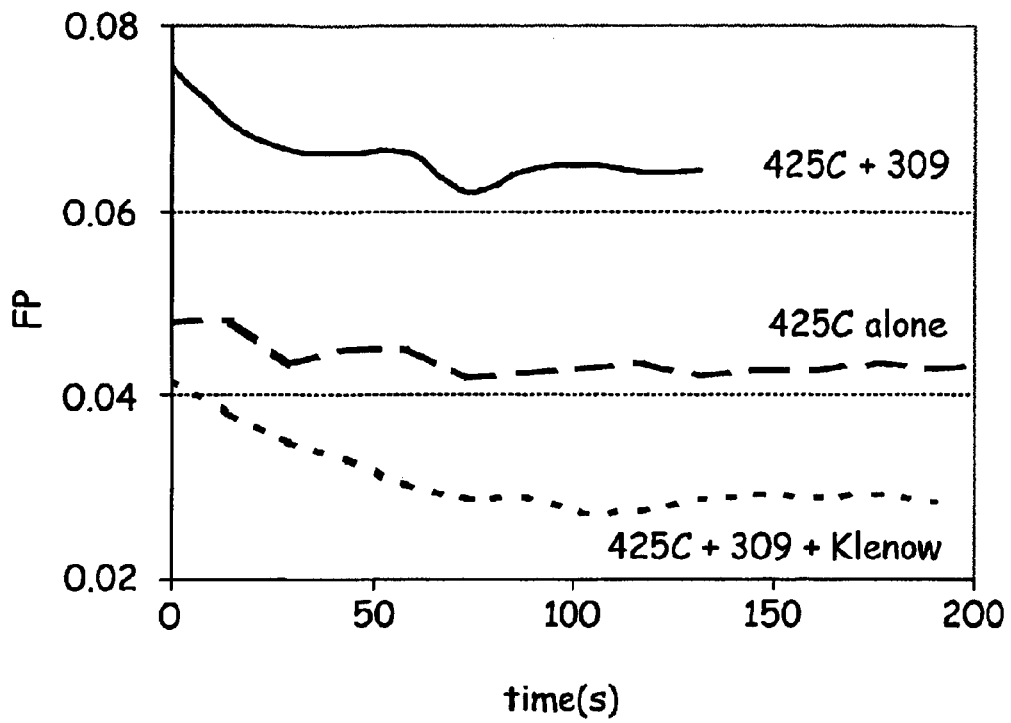
FIG. 5A is a plot of a probe that is perfectly matched to the target sequence in the extension reaction mixture (the 3' terminal base of the probe is complementary to the position of interest in the target sequence).
Figure 5B:
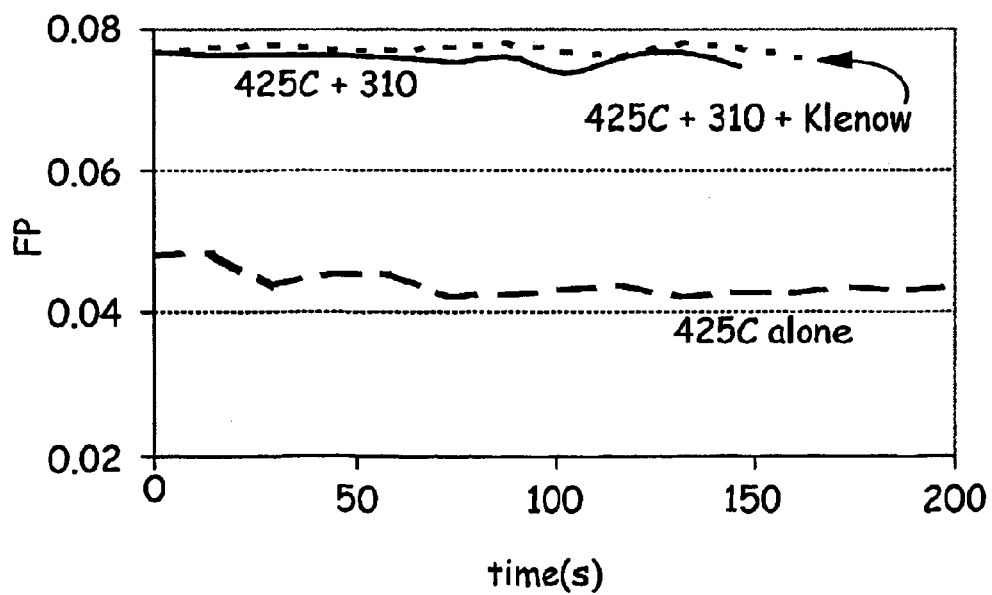
FIG. 5B illustrates the same plot for fluorescence polarization of an extension reaction mixture of a hybrid of a dye-labeled probe that is not perfectly complementary to the target sequence (contains a mismatch at the probe's 3' terminal position for the position of interest in the target sequence).

2. Hybridization and Enzymatic Extension Reactions: Use of Synthetic DNA Targets All hybridization and enzymatic extension reactions with the synthetic DNA targets were carried out in a buffer containing 25 mM Tris-HCl, pH 7.5, 10 mM $MgCl_2$, and 50 mM NaCl (referred to as "Klenow buffer"). In a typical experiment, 500 nM of a fluorescein labeled probe was dissolved in 400 µl of Klenow buffer and the fluorescence polarization and the total fluorescence intensity of the solution were measured on a Spex Fluoromax fluorometer. To the solution was then added 1 µM of a DNA target and the fluorescence intensity and polarization were again measured. Then, 1 µl of a solution containing all four deoxynucleoside triphosphates (dNTPs) was added, resulting in a final concentration of 25 µM of each of the four dNTPs. Finally, to the mixture was added 4 µm of a 10 u/µl stock solution of Klenow polymerase or its exonuclease-minus version. The final concentration of the polymerase in the extension solution was 0.01 u/µl. The polymerases were obtained from ChimerX (Madison, Wis.). Following the polymerase addition, the fluorescence polarization and total fluorescence intensity of the reaction mixture were followed for a period of several minutes. The results from the hybridization and polymerase extension experiments are shown in FIGS. 5A and 5B. Specifically, FIG. 5A illustrates primer extension reactions using the perfect match labeled probe 425C and target 309 (in the presence of 0.01 u/µl of Klenow polymerase). FIG. 5B illustrates the same reaction conditions for the CA mismatch of probe 425C and target 310.

As can be seen (FIG. 5A) fluorescence polarization decreases only in reaction that included the perfectly matched primer/target sequence, indicating that extension had occurred. The mismatched pair yielded no substantial change in fluorescence polarization, and thus no measurable primer extension (FIG. 5B).

3. Hybridization and Enzymatic Extension Reactions: Typing of PCR Products

Standard amplification protocols were used to generate a double-stranded PCR product, using the following synthetic DNA templates and PCR primers. The two targets differ on one position only, where target A has a G, and target B has an A:

Templates:
A.
5'CGCACCACTAGTGCCAATGGCACCAAAA-CACCCTTTGGCATgTAATGCC TAACATAATG-GCAGGGAGTTGCAAAGAGTAAGCACTTA (SEQUENCE ID NO:9)

B.
5'CGCACCACTAGTGCCAATGGCACCAAAA-CACCCTTTGGCATaTAATGCC TAACATAATG-GCAGGGAGTTGCAAAGAGTAAGCACTTA (SEQUENCE ID NO:10)

Primers:
5'TAAGTGCTTACTCTTTGCAAC (SEQUENCE ID NO:11)
5'<u>CGCAC</u>CACTAGTGCCAATGGC (SEQUENCE ID NO:12) (underlined bonds are phosphorothioates)

Figure 6A:
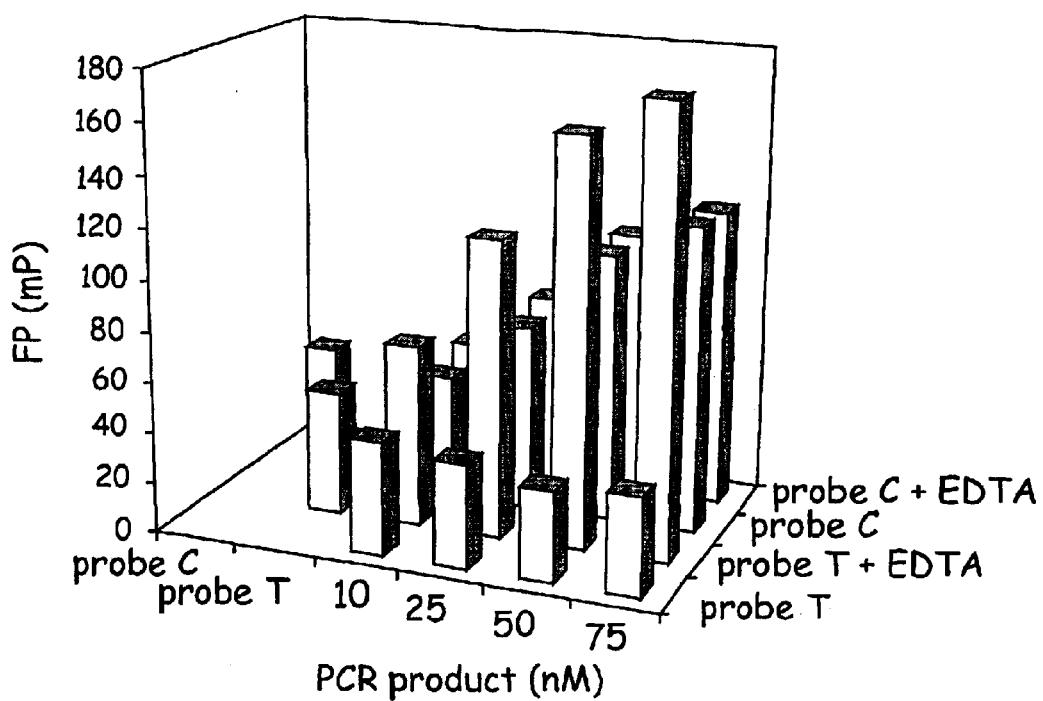
FIGS. 6A and 6B are plots of genotyping reactions for PCR products using the primer extension methods of the invention.
Figure 6B:
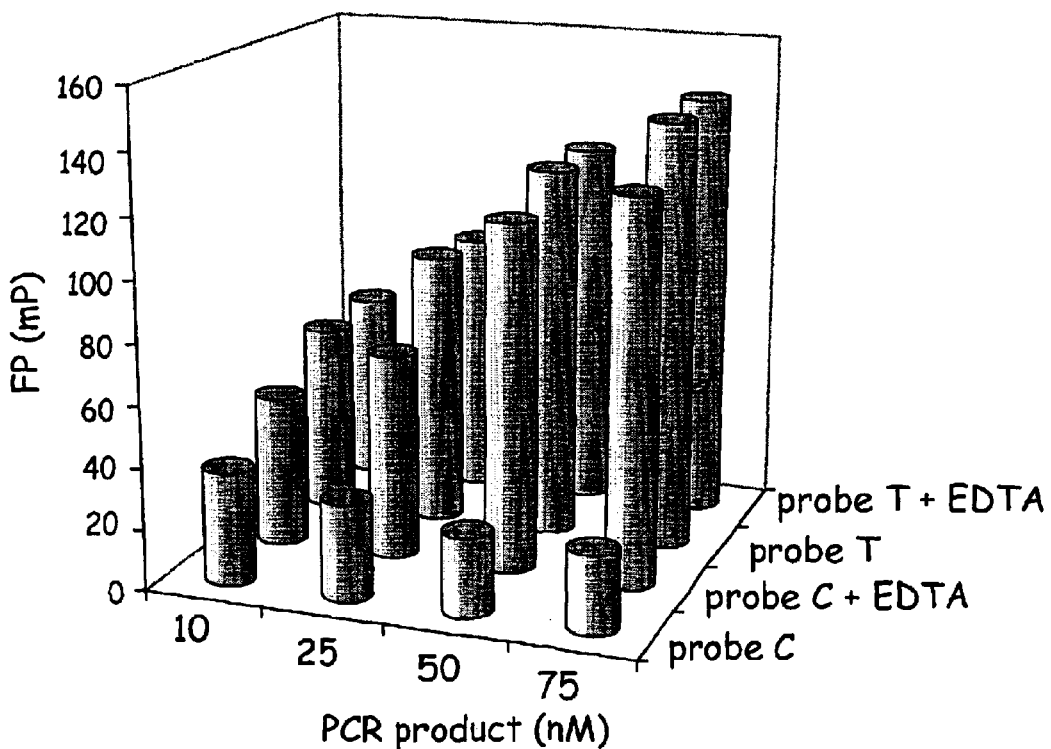

Following the amplification, the PCR products were quantified by gel electrophoresis and then treated with T7 gene 6 exonuclease to completely hydrolyze one of the PCR strands and generate a single-stranded PCR product. Then, increasing concentrations (10, 25, 50, and 75 nM) of the PCR products were mixed with the 3' fluorescein-labeled probes 425T or 425C. The final concentrations of these probes were 50 nM. The mixtures were heated to 95° C. for 2 minutes and allowed to cool to room temperature. The fluorescence polarization values of the mixtures were then recorded. In parallel experiments, to aliquots of the single stranded PCR products was added EDTA to a final concentration of 10 mM. The fluorescein labeled probes were then added and the mixtures processed as described above. These mixtures served as hybridization only controls, as the EDTA chelates the Mg2+ and no enzymatic extension can take place. The results are shown as column plots in FIGS. 6A and 6B. Specifically, synthetic DNA templates differing in one position only ("A" allele, FIG. 6A; "G" allele, FIG. 6B) were amplified, converted to single stranded products and hybridized, at four different concentrations, to 50 nM of probes 425T or 425C. To prevent polymerase extension, EDTA was added to some of the mixtures, to serve as hybridization controls. As can be seen from the plots each probe is extended only when hybridized to a completely matching PCR target. It is also notable that the primer extension was catalyzed by leftover Taq polymerase and excess dNTPs from the PCR amplification, yielding a simple one pot process.

Unless otherwise specifically noted, all concentration values provided herein refer to the concentration of a given component as that component was added to a mixture or solution independent of any conversion, dissociation, reaction of that component to alter the component or transform that component into one or more different species once added to the mixture or solution.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

What is claimed is:

1. A method of identifying a nucleotide in at least a first position in a polynucleotide sequence, comprising:

providing a polynucleotide target sequence;

hybridizing the target sequence with a first oligonucleotide probe, wherein:

the probe comprises a first subsequence of nucleotides, a first 3'-terminal nucleotide, and a first florescent label coupled to the 3'-terminal nucleotide;

the subsequence is complementary to a portion of the target sequence that is immediately adjacent to the first position; and the 3'-terminal nucleotide is complementary to one possible nucleotide in the first position;

contacting the hybridized probe and target sequence with polymerase extension reagents in a first extension reaction mixture;

measuring a level of polarized fluorescence emitted from the first extension reaction mixture, a decrease in polarized fluorescence indicating the presence of polymerase extension of the probe, the presence of polymerase extension of the probe indicating that the 3'-terminal nucleotide is complementary to the nucleotide in the first position; and identifying the nucleotide in the first position.

2. The method of claim 1, wherein the polymerase extension reagents include a 5'–3' DNA polymerase enzyme.

3. The method of claim 1, wherein the probe is from about 10 to about 50 nucleotides in length.

4. The method of claim 1, wherein the subsequence is from about 9 to about 49 nucleotides in length.

5. The method of claim 1, wherein the polymerase extension reagents comprise a non-proofreading polymerase.

6. The method of claim 5, wherein the non-proofreading polymerase is selected from exonuclease minus klenow fragment, Taq polymerase, and Thermosequenase.

7. The method of claim 1, wherein the contacting step occurs in a channel of a microfluidic device.

8. The method of claim 1, further comprising:

hybridizing the target sequence with a second oligonucleotide probe that comprises:

the first subsequence of nucleotides, a second 3'-terminal nucleotide, and a second florescent label coupled to the second 3'-terminal nucleotide, the second fluorescent label being distinguishable from the first fluorescent label; and the second 3'-terminal nucleotide is different from the first 3'-terminal nucleotide and is complementary to one possible nucleotide in the first position; and wherein the measuring step comprises measuring a level of polarized fluorescence emitted from each of the first and second fluorescent labels, a decrease in the amount of polarized fluorescence from one of the first and second fluorescent labels being indicative of polymerase extension of the first or second oligonucleotide probe, respectively.

9. A method for identifying a nucleotide in a first position in a target nucleic acid sequence, comprising:

amplifying the target nucleic acid sequence in a first reaction mixture that includes effective amounts of polymerase enzyme and four dNTPs;

introducing into the first reaction mixture a first primer sequence to produce a second reaction mixture under conditions conducive to a polymerase mediated primer extension, wherein the first primer sequence comprises a first subsequence of nucleotides, a first 3'-terminal nucleotide, and a first florescent label coupled to the 3'-terminal nucleotide, wherein the subsequence is complementary to a portion of the target sequence that is immediately adjacent to the first position, and the first 3'-terminal nucleotide is complementary to one possible nucleotide in the first position;

measuring a level of polarized fluorescence emitted from the second reaction mixture, a decrease in amount of polarized fluorescence being indicative of the presence extension of the first primer sequence, the presence of polymerase extension of the first primer sequence indicating that the 3'-terminal nucleotide is complementary to the nucleotide in the first position; and identifying the nucleotide in the first position.

\* \* \* \* \*

SEQUENCE LISTING

<160> NUMBER OF SEQ ID NOS: 12

<210> SEQ ID NO 1
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: Fluorescein labeled thymidine residue

<400> SEQUENCE: 1
ctgccattat gttaggcatt an                                              22

<210> SEQ ID NO 2
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: Fluorescein labeled cytosine residue

<400> SEQUENCE: 2
ctgccattat gttaggcatt an                                              22

<210> SEQ ID NO 3
<211> LENGTH: 22
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: fluorescein labeled thymidine residue

<400> SEQUENCE: 3
aggacttcca cgtggaccag gn                                              22

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (22)..(22)
<223> OTHER INFORMATION: fluorescein labeled thymidine residue
<220> FEATURE:
<221> NAME/KEY: misc_feature
<222> LOCATION: (23)..(23)
<223> OTHER INFORMATION: fluorescein labeled cytosine residue

<400> SEQUENCE: 4
aggacttcca cgtggaccag gnn                                             23

<210> SEQ ID NO 5
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 5
tttggcatgt aatgcctaac ataatggcag                                       30

<210> SEQ ID NO 6
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 6
tttggcatat aatgcctaac ataatggcag                                       30

<210> SEQ ID NO 7
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 7
acggtggtcg cctggtccac gtggaagtcc t                                     31

<210> SEQ ID NO 8
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 8
acggtggtca cctggtccac gtggaagtcc t                                     31

<210> SEQ ID NO 9
<211> LENGTH: 87
<212> TYPE: DNA
<213> ORGANISM: Artificial sequence
<220> FEATURE:
<223> OTHER INFORMATION: Synthetic oligonucleotide

<400> SEQUENCE: 9
cgcaccacta gtgccaatgg caccaaaaca ccctttggca tgtaatgcct aacataatgg      60
cagggagttg caaagagtaa gcactta                                          87

<210> SEQ ID NO 10
<211> LENGTH: 87
<212> TYPE: DNA
<213> ORGANISM: Artificial sequence
<220> FEATURE:
<223> OTHER INFORMATION: Synthetic oligonucleotide

<400> SEQUENCE: 10
cgcaccacta gtgccaatgg caccaaaaca ccctttggca tataatgcct aacataatgg      60
cagggagttg caaagagtaa gcactta                                          87

<210> SEQ ID NO 11
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 11

-continued

```
taagtgctta ctctttgcaa c                                        21

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
cgcaccacta gtgccaatgg c                                        21
```